United States Patent

Baker et al.

(10) Patent No.: US 9,882,610 B1
(45) Date of Patent: Jan. 30, 2018

(54) NEAR FIELD COMMUNICATION SENSOR SYSTEM

(71) Applicant: Welch Allyn, Inc., Skaneateles Falls, NY (US)

(72) Inventors: Steven D. Baker, Beaverton, OR (US); Michael Scott Hood, Batesville, IN (US)

(73) Assignee: WELCH ALLYN, INC., Skaneateles Falls, NY (US)

(*) Notice: Subject to any disclaimer, the term of this patent is extended or adjusted under 35 U.S.C. 154(b) by 0 days.

(21) Appl. No.: 15/346,361

(22) Filed: Nov. 8, 2016

(51) Int. Cl.
| | |
|---|---|
| *H04B 5/00* | (2006.01) |
| *H04W 76/02* | (2009.01) |
| *A61B 5/00* | (2006.01) |
| *A61G 7/05* | (2006.01) |
| *H04W 4/00* | (2009.01) |

(52) U.S. Cl.
CPC .......... *H04B 5/0043* (2013.01); *A61B 5/002* (2013.01); *A61G 7/0524* (2016.11); *H04B 5/0037* (2013.01); *H04W 76/023* (2013.01); *H04W 4/008* (2013.01)

(58) Field of Classification Search
CPC .......................... H04B 5/0043; H04B 5/0037
See application file for complete search history.

(56) References Cited

U.S. PATENT DOCUMENTS

| | | | |
|---|---|---|---|
| 5,561,412 A | 10/1996 | Novak et al. | |
| 8,082,160 B2 | 12/2011 | Collins, Jr. et al. | |
| 8,120,471 B2 | 2/2012 | Collins, Jr. et al. | |
| 8,756,078 B2 | 6/2014 | Collins, Jr. et al. | |
| 8,984,685 B2 | 3/2015 | Robertson et al. | |
| 9,356,661 B2 | 5/2016 | Samardzija et al. | |
| 9,397,385 B2 | 7/2016 | McFarthing | |
| 2003/0181791 A1* | 9/2003 | Thomas | A61B 5/05 600/300 |
| 2004/0021467 A1* | 2/2004 | Eberler | G01R 33/34007 324/318 |
| 2007/0118054 A1 | 5/2007 | Pinhas et al. | |
| 2013/0091631 A1 | 4/2013 | Hayes et al. | |
| 2013/0135160 A1 | 5/2013 | Dixon et al. | |

(Continued)

FOREIGN PATENT DOCUMENTS

| | | |
|---|---|---|
| CN | 103623480 A | 3/2014 |
| CN | 203634563 U | 6/2014 |

(Continued)

OTHER PUBLICATIONS

Bravo, J. et al., "Enabling NFC technology in hospital wards," 7 pages (Jan. 2009).

(Continued)

*Primary Examiner* — Tuan H Nguyen
(74) *Attorney, Agent, or Firm* — Merchant & Gould P.C.

(57) ABSTRACT

A sensor system includes a person-supporting device with an antenna and a near-field communication (NFC) interrogation device. A first sensor is configured to measure a physiological parameter of a patient associated with the person-supporting device, and the NFC interrogation device and the antenna are configured to establish wireless communication with the first sensor and receive data from the first sensor from a distance of at least 10 inches.

17 Claims, 6 Drawing Sheets

(56) References Cited

U.S. PATENT DOCUMENTS

| | | | |
|---|---|---|---|
| 2013/0271278 A1* | 10/2013 | Duesterhoft | A61B 5/002 340/539.12 |
| 2014/0020175 A1 | 1/2014 | Dixon et al. | |
| 2014/0225746 A1 | 8/2014 | Nagase et al. | |
| 2014/0240184 A1* | 8/2014 | Andle | G01R 29/0871 343/720 |
| 2014/0297310 A1 | 10/2014 | Collins, Jr. et al. | |
| 2014/0297327 A1 | 10/2014 | Heil et al. | |
| 2015/0077268 A1 | 3/2015 | Lane et al. | |
| 2015/0082542 A1 | 3/2015 | Hayes et al. | |
| 2017/0027515 A1* | 2/2017 | Wiser | A61B 5/6833 |

FOREIGN PATENT DOCUMENTS

| | | |
|---|---|---|
| CN | 104077906 A | 10/2014 |
| WO | 2014/043659 A1 | 3/2014 |
| WO | 2014/150970 A1 | 9/2014 |
| WO | 2014/151577 A1 | 9/2014 |

OTHER PUBLICATIONS

Hayn, D. et al., "An eHealth System for Pressure Ulcer Risk Assessment Based on Accelerometer and Pressure Data," Journal of Sensors, vol. 2015, Article ID 106537, 9 pages (Copyright 2015).

Milenkovic, A. et al., "Smartphones for Smart Wheelchairs," IEEE International Conference Body Sensor Networks (BSN), 6 pages (2013).

\* cited by examiner

NEAR FIELD COMMUNICATION SENSOR SYSTEM

INTRODUCTION

Wireless sensors are used in a variety of applications. In hospital and other healthcare facilities, wearable body sensors can be used to efficiently monitor a patient's physiological parameters or vital signs, such as body temperature or heartbeat, in various situations. The sensor generally includes functionality for taking and storing the desired patient information, as well as an antenna for receiving and transmitting the information. Data thus can be transmitted from the sensor device to an interrogation device, which may be implemented by various devices such as smartphones, tablets, wearable devices, or other independent devices such as bedside medical devices. Near-field communication (NFC) devices may be used in such sensor systems, which involve electromagnetically coupled communications over short distances. The interrogation device may be held or worn by a caregiver, patient or other individual having an interest in the operation of the sensing device, and accordingly tend to be small devices.

SUMMARY

Examples of a sensor system disclosed herein include a person-supporting device that includes an antenna and a near-field communication (NFC) interrogation device. A first sensor is configured to measure a physiological parameter of a patient associated with the person-supporting device, and wherein the NFC interrogation device and the antenna are configured to establish wireless communication with the first sensor and receive data from the first sensor from a distance of at least 10 inches. The person-supporting device could include, for example, a bed, stretcher, exam table, operating table, office chair, automobile seat or other platform having a substrate or support upon which the NFC interrogation device and antenna are mounted. Such a substrate may then be placed near a monitored person, such as on a wheel chair or bed. In some examples, the person-supporting device includes a bed with the antenna integrated into the bed.

DESCRIPTION OF THE FIGURES

The following figures, which form a part of this application, are illustrative of described technology and are not meant to limit the scope of the claims in any manner, which scope shall be based on the claims appended hereto.

DETAILED DESCRIPTION

Figure 1:
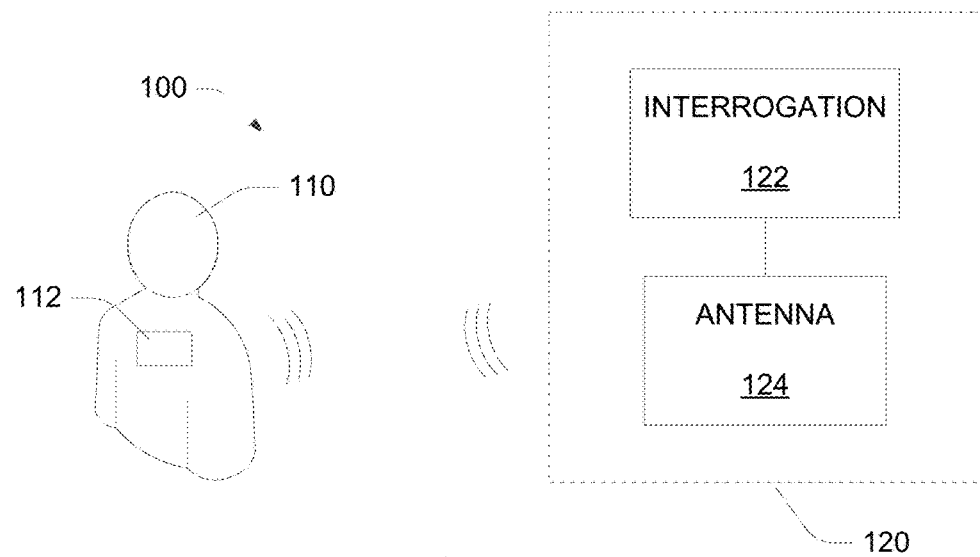
FIG. 1 is a block diagram conceptually illustrating aspects of an example sensor system.

In the following detailed description, references are made to the accompanying drawings that form a part hereof, and in which are shown by way of illustrations specific embodiments or examples. These aspects may be combined, other aspects may be utilized, and structural changes may be made without departing from the spirit or scope of the present disclosure. The following detailed description is therefore not to be taken in a limiting sense.

In general, a sensor system in accordance with the present disclosure operates to detect a physiological parameter of a patient using a sensing device, and receive and monitor data regarding the measured parameter using an interrogation device. An interrogation device is sometimes referred to as a reader, as in "an NFC reader." In this specification, when NFC or RFID is used, it refers not necessarily to a specific ISO standard, but more generally to the concept of providing a signal to a remote device, causing the remote device to transmit back a signal to the reader. Near-field may be considered to include distances where changing the EM environment around a transmitter affects the radiation pattern far from the object. The remote device may use none, some, or all of the received energy from the transmitter to support transmission of a data back to the reader. The received energy may be coupled through at least electromagnetic means (inductive, capacitive, RF) optically, or mechanically. The sensing device, for example, could be a sensor that contacts or is worn by the patient and configured to measure a desired attribute associated with a patient, such as temperature, oxygen saturation level (SpO2), blood pressure (BP), end tidal carbon dioxide (ETCO2), heart rate, body position, motion, acceleration, and respiration rate. A caregiver or other concerned party then may record the sensor output to monitor the measured patient parameters. Some contact sensors include a measurement read out, such as a temperature sensor that provides a visual indication of the patient's measured temperature, which may be read and recorded by a caregiver. Other sensors may provide indication of use of nearby medical equipment, for example use of suction, a defibrillator, hand cleansing or use of medical consumable products such as gloves, sponges, various probe covers, and the like.

In implementations where a sensor is to contact or be worn by a patient, it may be desirable for the sensor device to be as small as possible so as to be more comfortable for the patient. Among other things, eliminating a wired battery charger interface, or eliminating the battery or other larger power source altogether would allow reducing the size of the sensor. Eliminating a data read-out user interface and/or an interface for a wired data connection for transferring information from the sensor to an interrogation device further allows reducing the size of the sensor.

To this end, some sensor systems use near-field communication (NFC), which is a technology that provides a low power solution in which a battery or wired battery charger interface is not required for the sensor. For example, an NFC transmitter-receiver ("transceiver") may use an NFC communications antenna to transmit and receive near-field electromagnetic signals at a frequency such as 125-134.2 kHz (LF), 13.56 MHz (HF), 860-960 MHz (UHF), and 2.45 GHz (SHF). Other frequencies may be used. These devices employ electromagnetic coupling between near-field antennas associated with the sensor and interrogation device to both power the sensor and read data from the sensor. Such NFC solutions are often implemented in small hand-held devices which require a clinician to be very close (within a few inches) of the patient's sensor to read and power the sensor when using HF systems and small antennas, but up to one meter with large antennas. UHF systems can read at a longer range of up to 15 meters, but a UHF tag can be created to read in the near field only. Battery assisted tags UHF tags can have a read-range up to 50 meters.

Positioning the NFC interrogation device so close to the patient's sensor so as to accommodate typical hand-held or smart-phone supported NFC readers may not always be practical or even possible. For instance, if a patient positioned in a bed such that the sensor is located between the patient and the mattress, it might not be possible to position a typical NFC interrogation device close enough to the sensor to achieve the required electromagnetic coupling.

Figure 2:
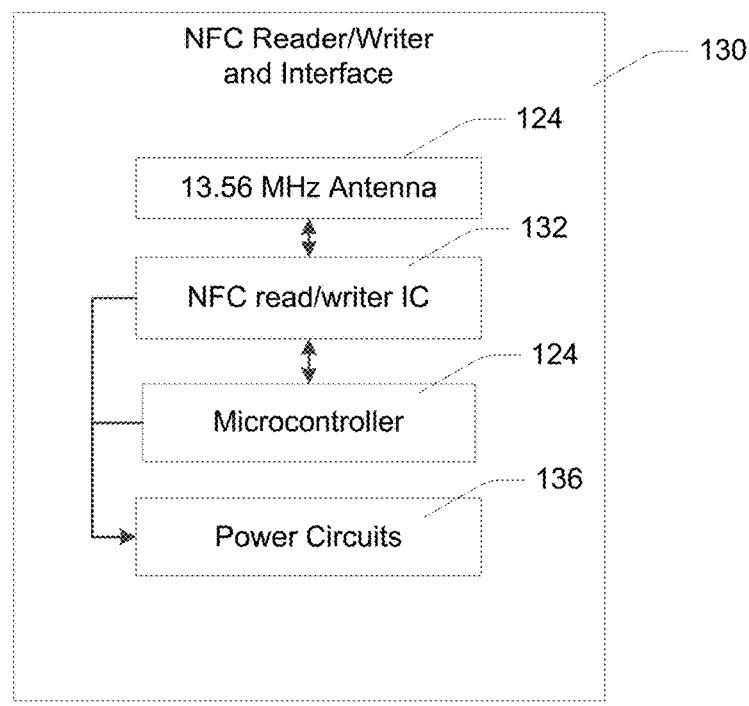
FIG. 2 is a block diagram illustrating an example of a near-field communication (NFC) device suitable for use with the interrogation device shown in FIG. 1.

FIG. 1 conceptually illustrates aspects of an example sensor system 100 using NFC devices. In the illustrated example, a physiological parameter or attribute of a patient 110 is monitored using a sensor 112 that is configured to measure the desired physiological parameter. A person-support device 120 is associated with the patient 110, and includes a near-field communication (NFC) interrogation device 120 and antenna 122. FIG. 2 shows an example NFC device 130 incorporated with the interrogation device 120, which includes an NFC read/write IC 132 connected to the antenna 124, along with a microcontroller 134 and power circuits 136. Tuning may be accomplished by various means such as changing the size of the antenna, the number of windings, the spacing between the windings, the adjacent ground structure, adding bulk elements including capacitors, inductors and resistors, and the like. Typically, antennas are tuned to match the transmission/reception frequency.

Figure 3:
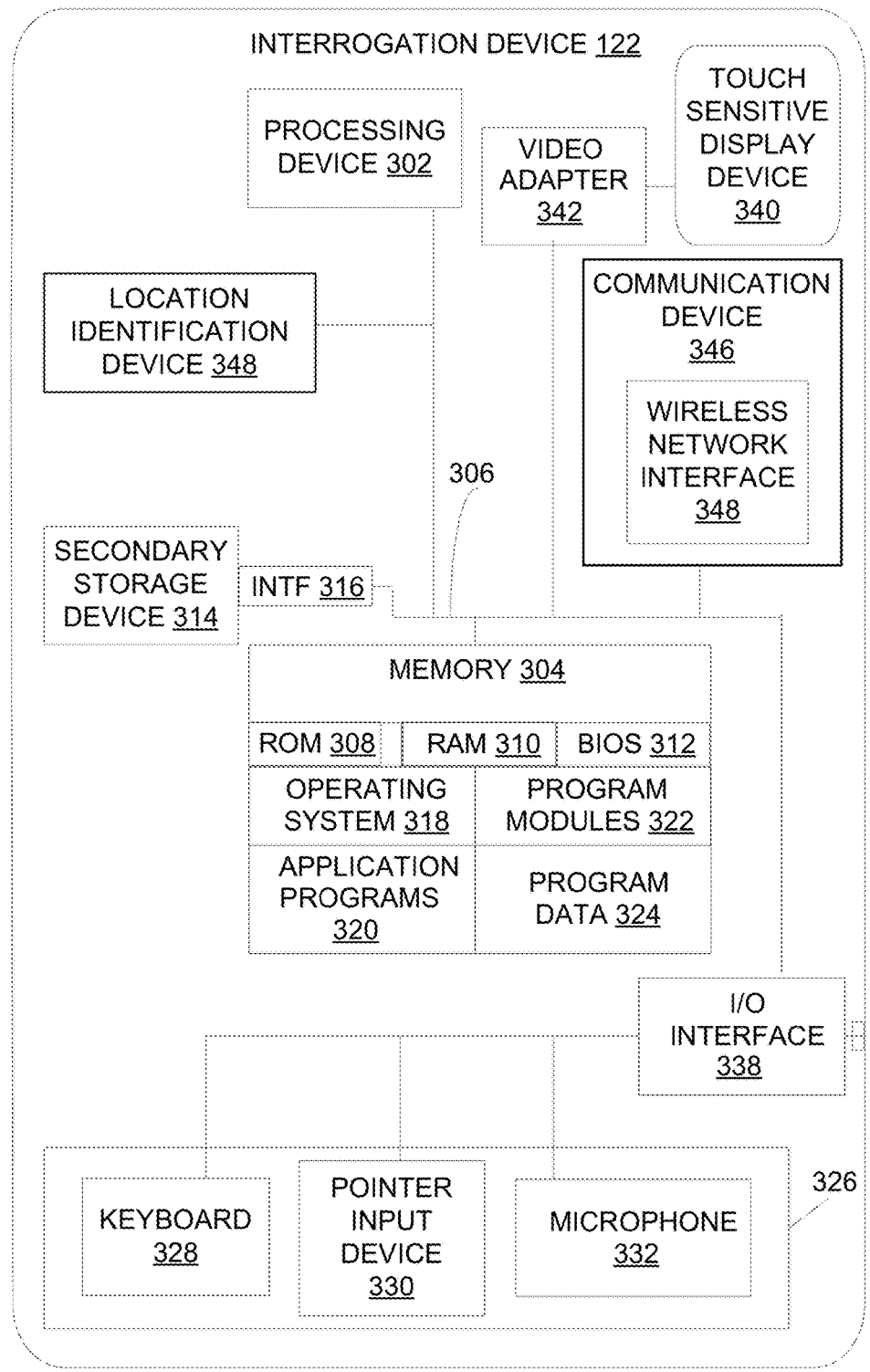
FIG. 3 is a block diagram illustrating an example of an interrogation device.

FIG. 3 illustrates further aspects of an example interrogation device 120. The interrogation device 122 includes, in some embodiments, at least one processing device 302, such as a central processing unit (CPU). A variety of processing devices are available from a variety of manufacturers, for example, Intel or Advanced Micro Devices. In this example, the interrogation device 122 also includes a system memory 304, and a system bus 306 that couples various system components including the system memory 304 to the processing device 302. The system bus 306 is one of any number of types of bus structures including a memory bus, or memory controller; a peripheral bus; and a local bus using any of a variety of bus architectures.

The system memory 304 includes read only memory 308 and random access memory 310. A basic input/output system 312 containing the basic routines that act to transfer information within the interrogation device 122, such as during start up, is typically stored in the read only memory 308.

The interrogation device 122 also includes a secondary storage device 314 in some embodiments, such as a hard disk drive, for storing digital data. The secondary storage device 314 is connected to the system bus 306 by a secondary storage interface 316. The secondary storage devices and their associated computer readable media provide nonvolatile storage of computer readable instructions (including application programs and program modules), data structures, and other data for the interrogation device 122.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 314 or memory 304, including an operating system 318, one or more application programs 320, other program modules 322, and program data 324. Some embodiments may include an EHR/EMR interface that allows the interrogation device to read and write data to/from the patient's medical record.

In some embodiments, the interrogation device 122 includes input devices to enable a user to provide inputs to the interrogation device 122. Examples of input devices 326 include a keyboard 328, a pointer input device 330, a microphone 332, and a touch sensitive display 340. Other embodiments include other input devices. The input devices are often connected to the processing device 302 through an input/output interface 338 that is coupled to the system bus 306. These input devices 326 can be connected by any number of input/output interfaces, such as a parallel port, serial port, game port, or a universal serial bus. Wireless communication between input devices and interface 338 is possible as well, and includes infrared, acoustic (including ultrasonic), ultra wideband, BLUETOOTH® wireless technology, 802.11a/b/g/n/ac/ad, PCE, cellular, or other radio frequency communication systems in some possible embodiments.

In this example embodiment, a touch sensitive display device 340 is also connected to the system bus 306 via an interface, such as a video adapter 342. The touch sensitive display device 340 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 340, the interrogation device 122 can include various other peripheral devices (not shown), such as speakers or a printer.

The computing device 300 further includes a communication device 346 configured to establish communication across a network, such as a hospital network or the internet. In some embodiments, when used in a local area networking environment or a wide area networking environment (such as the Internet), the computing device 300 is typically connected to the network through a network interface, such as a wireless network interface 348. Other possible embodiments use other wired and/or wireless communication devices. For example, some embodiments of the computing device 300 include an Ethernet network interface, or a modem for communicating across the network. As noted above, the interrogation device 122 includes an NFC communication device. In yet other embodiments, the communication device 346 is capable of additional wireless communications, such radio frequency identification (RFID), Bluetooth technology, Wi-Fi technology, etc. The interrogation device 122 and antenna 124 may be located separately. Combinations of RF solutions may be included, for example using NFC to transfer and/or confirm link information such as radio address and encryption keys for WiFi or Bluetooth.

The interrogation device 122 typically includes at least some form of computer-readable media. Computer readable media includes any available media that can be accessed by the interrogation device 122. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the interrogation device 122. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

Figure 4:
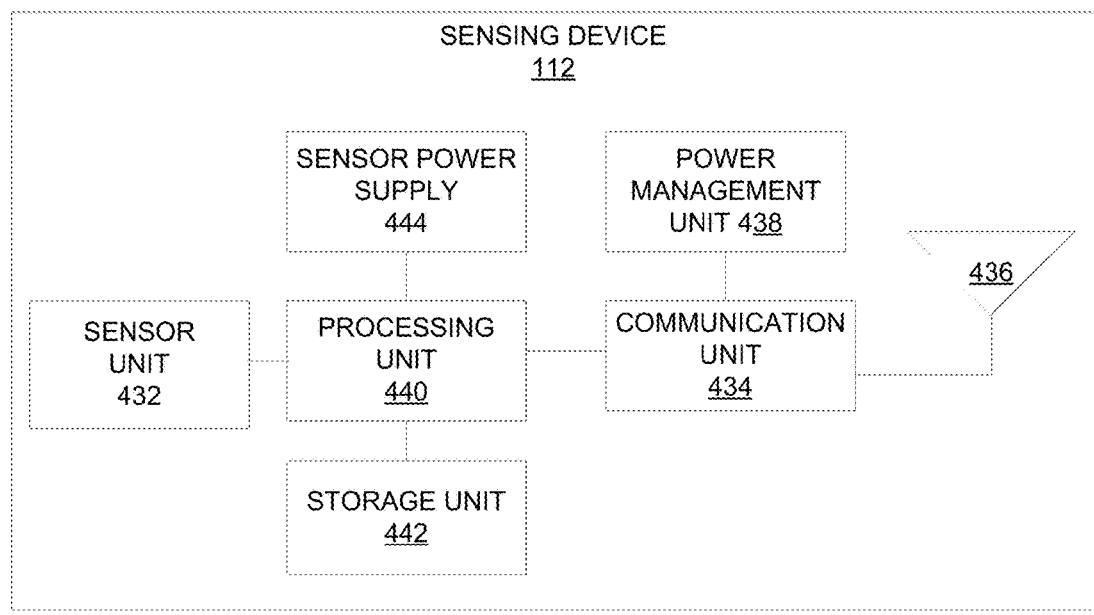
FIG. 4 a block diagram illustrating an example of a block diagram illustrating an example of a sensing device.

FIG. 4 schematically illustrates aspects of an example of the sensing device 112, which is used to measure physiological parameters of the patient 110. In the illustrated example, the sensing device 112 includes a sensor unit 432, a communication unit 434, an antenna 436, a power management unit 438, a processing unit 440, a storage unit 442, and a sensor power supply 444. In other embodiments, the sensing device 112 can include one or more components in addition to the components described above, and/or replace one or more of the components described above by different components. In some examples, the sensing device 112 is at least partially implemented in an integrated circuit.

The sensor unit 432 includes one or more sensors operable to detect one or more physiological parameters or patient attributes, such as position, falls, location, body angle, and the like. Position, for example, may be determined without a specific dedicated sensor by positioning an antenna's read range to detect the presence or non-presence of a tag. Similarly, velocity may be determined by measuring the time elapsed between readings by two antennas separated by a known distance. In some examples, the sensor unit 432 includes one sensor for detecting one type of physiological parameters. In other examples, the sensor unit 432 includes a plurality of sensors for detecting different types of physiological parameters. Example sensors of the sensor unit 432 include temperature sensors, heartrate sensors, electrocardiogram (ECG) sensors, respiratory rate sensors, accelerometers, SpO2 sensors, heartrate variability sensors, galvanic skin response sensors, blood pressure sensors, blood glucose sensors, blood oxygen sensors, blood chemistry sensors, breath analysis sensors, and any other sensors suitable for measuring physiological parameters. The sensor unit 432 can further include one or more sensors (e.g., accelerometer) for detecting the subject's activity and posture, such as whether the subject is standing, sitting, laying down, or engaged in physical activity, such as running. In some examples, the sensor unit 432 is powered by the sensor power supply 444.

The communication unit 434 configured as an interface suitable for communicating with the interrogation device 122 via NFC technology. In some examples, the communication unit 434 can receive signals from the interrogation device 122 via the wireless communication link 348 and transmit data to the interrogation device 122. The antenna 436 is configured as an NFC antenna to receive and transmit a radio frequency (RF) signal. In some examples, the antenna 436 is made flat so as to be incorporated into the sensing device 112. Other configurations are also possible in other embodiments. The sensor might have local power assistance where a local power source such as a battery or energy harvester such as a thermopile, mechanical, or solar provides some of the energy required to transmit a response. The sensor might use an NFC or RFID detection as a trigger or interrupt to cause a different radio to transmit data. For example, a system might have a Bluetooth LE beacon capability and transmission of the beacon is triggered by detection of an NFC/RFID reader instead of using the typical Bluetooth protocols for detection. Other activation methods such as motion from tapping on the sensor as a non-limiting example may be detected by an accelerometer or gyro, voice command (detected by a TI RF4CE solution), detection of an another person in the room, optical detection, detection of other RF signal events, or other method that indicates there is a need to provide the data. Detection of a person in the room might include an interface to existing systems, for example the Hill-Rom Hand Hygiene Compliance Solution that uses badge-based locating technology. When a clinician is detected entering the room by the Hand Hygiene Compliance Server (HHCS), the HHCS commands a second server that supervises beds to energize the RFID reader. The system might use a timed solution where it makes a measurement at prescribed intervals. The prescribed intervals might vary as a function of how the measurement has trended. For example, if temperature recently increased from 37 C to 38 C between measurements, then the time between measurements might decrease. The device may also receive instructions to change the prescribed interval.

The power management unit (PMU) 438 operates to harvest raw RF power received via the antenna 436. In particular, an RF wave received via the antenna 436 is transmitted to the PMU 438 as a signal. Harvested energy may be used for the instant measurement or stored for later measurements. The signal is used for harvesting the power and also decoded for further processes. The sensing device 112 then uses the power to respond as necessary in response to the incoming signal from the interrogation device 122. Many of the functional blocks, such as 434, 438, 440, 442, and 444 may be incorporated into single integrated circuits, such as the Texas Instruments SCBUO46 or RF430FRL15xH devices. The latter has an A/D convertor, temperature sensor, an I2C interface to support external sensors and can be powered by a battery and activated by an external magnetic field or completely powered by an external magnetic field.

In some examples, in the communication between the sensing device 112 and the interrogation device 122, the sensing device 112 operates as a passive NFC device. In this configuration, the sensing device 112 does not consume power from internal power source, such as the sensor power supply 444, for communication with the interrogation device 122. Instead, when interrogated by the interrogation device 122, the sensing device 112 can be powered by electromagnetic induction from magnetic fields produced near the interrogation device 122. However, it is recognized that the sensing device 112 can be powered in different manners, including during the communication with the interrogation device 122.

The processing unit 440 operates to control the sensor unit 432 and other components in the sensing device 112. Further, the processing unit 440 operates to communicate with the interrogation device 122. In some examples, the processing unit 440 receives signals from the antenna 436. In some examples, a modem (modulator/demodulator) is provided as part of the communication unit 434 to demodulate an RF signal received via the antenna 436 and modulate an RF signal transmitted via the antenna 436. The demodulator can be implemented in a way known in the art, including, for example, attenuator stage and amplifier stage. The processing unit 440 can perform various operations and generate an output signal for transmission. In some examples, a modulator is provided to modulate an output signal generated by the processing unit 440. The modulated signal is transmitted through the antenna 436 to the interrogation device 122. The modulator can be implemented in a way known in the art, including, for example, driver stage and amplifier stage. The processing unit 228 can be implemented in a way known in the art, including, for example, a processor, a decoder, and an encoder.

The storage unit 442 includes one or more memories configured to store the sensing device data. As described herein, the sensing device data can contain physiological parameter data obtained from the sensor unit 432 and other data associated with the sensing device 112 and/or the patient 110. The storage unit 442 can be of various types, including volatile and nonvolatile, removable and non-removable, and/or persistent media. In some embodiments, the storage unit 442 is an erasable programmable read only memory (EPROM). In other embodiments, the storage unit 442 might be implemented using FLASH or FRAM, The sensor power supply 444 is included in the sensing device 112 and provides power to operate the sensor unit 432 and associated elements, such as the processing unit 440 and the storage unit 442. In some examples, the sensor power supply 444 includes one or more batteries, which is either for single use or rechargeable. Batteries may be charged through a cabled connection or wirelessly, including through harvesting RF energy from interrogation device 122, Qi wireless transmission standard, or other harvesting means including thermopiles, solar, mechanical, and the like.

The person-supporting device 120 could include, for example, a patient bed, a patient lift, wheel chair, or other platform larger than a typical handheld device (smartphone, tablet, etc.). As noted above, the interrogation device 122 electromagnetically couples with the sensor 112. The person-supporting device 120 provides a larger platform, allowing the use of a larger power source and larger antenna, thus increasing the usable range beyond the typical few includes of standard NFC devices. In some embodiments, the antenna includes a conductive coil defining a semi-major axis of at least 0.01 wavelengths at 13.56 MHz enabling the interrogation device 122 to electromagnetically couple with the sensor 112 from distances of 15 cm up to 1 m, depending on the transmitting power of the interrogator. Ideally, the effective isotropic radiated power of the interrogator is minimized as large power transmissions may result in emissions that exceed the RF immunity test limits for medical devices, e.g. 3 V/m for electric fields, as well as limits to human exposure to RF.

Figure 5:
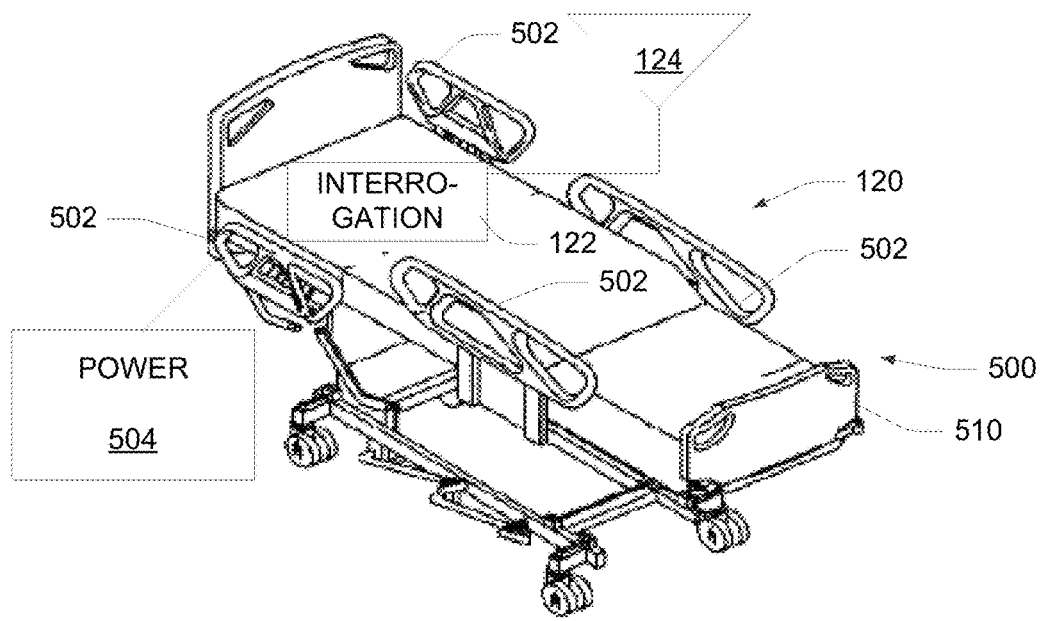
FIG. 5 illustrates an example person-supporting device including a bed.

FIG. 5 illustrates and example where the person-supporting device 120 includes a bed 500. In the illustrated example, the interrogation device 122 is integrated into the bed, which is connected to a power supply 504 for powering the interrogation device 122 as well as other components of the bed 500, such as a data uplink or backhaul (not shown). The interrogation device 122 may be either permanently mounted to the person-supporting device 120, semi-permanently mounted to the person-supporting device 120 (requiring tools to remove), or temporarily mounted (not requiring tools to remove) to the person-supporting device 120. An example of a temporary mount includes hanging from an IV pole, such as Hill-Rom Infusion Support System, product ISS 158. The interrogation 122 device may be mounted separately from the person-supporting device 120. Similarly, the antenna 124 may be permanently or semi-permanently mounted and it may be mounted inside the structure of the person supporting device 120 or affixed to an external surface. Permanent mounting includes manufacturing the person-supporting device 120 with at least one antenna 124 inside some portion of the person-supporting device 120.

Figure 6:
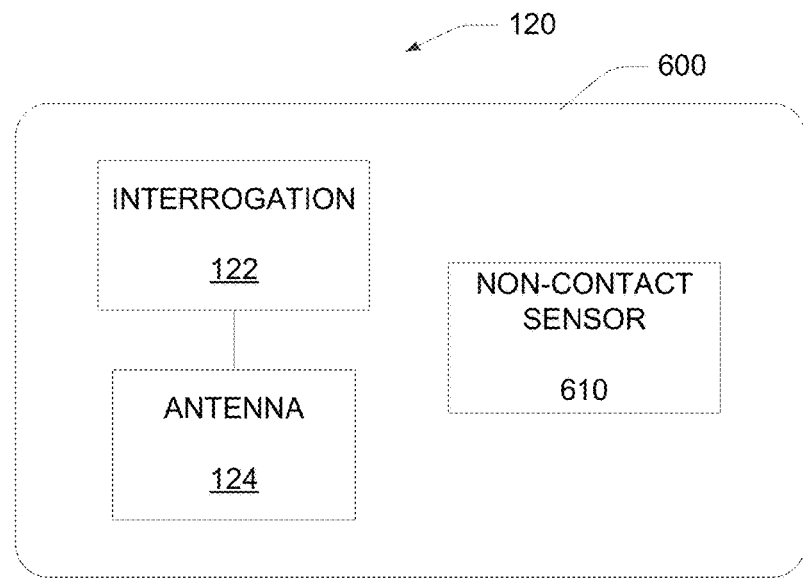
FIG. 6 illustrates another example of a person-supporting device where the interrogation device and antenna are mounted on a substrate.
Figure 7:
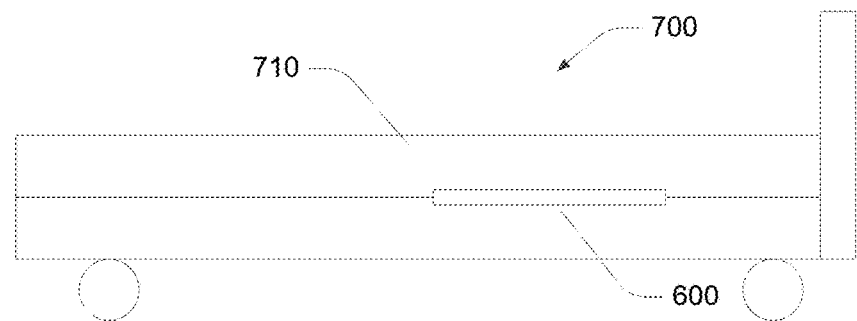
FIG. 7 illustrates an example of a person-supporting system where the substrate shown in FIG. 6 is received in a bed.

FIG. 6 illustrates another example in which the interrogation device 122 is mounted on a substrate 600 configured to be placed near the patient 110. In some embodiments, the interrogation device is integrated with a patient support system such as the EarlySense System manufactured by EarlySense of Waltham, Mass. Aspects of that system are described in U.S. patent application Ser. No. 11/552,872 filed on Oct. 25, 2006, which is incorporated by reference herein. Other devices can be used. In the example shown in FIG. 6, the interrogation device 122 and antenna 124 are mounted on the substrate 600. In other embodiments, the antenna 124 is mounted on the substrate and the interrogation device 122 is remote, for example, cabled from another location on the patient support structure. Additionally, some embodiments include a contactless sensor 610 that is configured to measure a physiological parameter of the patient without contacting the patient. The substrate 600 is suitable for placing near the patient 110 to measure and monitor physiological parameters (such as acceleration, motion, and orientation). As shown in FIG. 7, the substrate 600 may be positioned on a patient bed 700, such as under a mattress 710 of the bed. While placement under a mattress could be too far away from a patient worn sensor for operation using a conventional NFC system, the larger platform of the substrate 600 allows for a larger antenna and thus increased interrogation range. Antenna size is often measured in wavelengths, where the free space wavelength is the speed of light divided by the frequency of the electromagnetic radiation. The substrate device 600 may be either permanently mounted to the person-supporting device 120, semi-permanently mounted to the person-supporting device 120 (requiring tools to remove), or temporarily mounted (not requiring tools to remove) to the person-supporting device 120. The antenna may be either permanently mounted to the substrate device 600, semi-permanently mounted to the substrate device 600 (requiring tools to remove), or temporarily mounted (not requiring tools to remove) to the substrate device 600. If an existing substrate device has power and communication, the substrate device may provide power and/or data backhaul for the interrogation device.

Referring back to FIG. 5, in some implementations, the bed 500 includes a plurality of bedrails 502 that are spaced apart from one another and extend from the bed 500.

Figure 8:
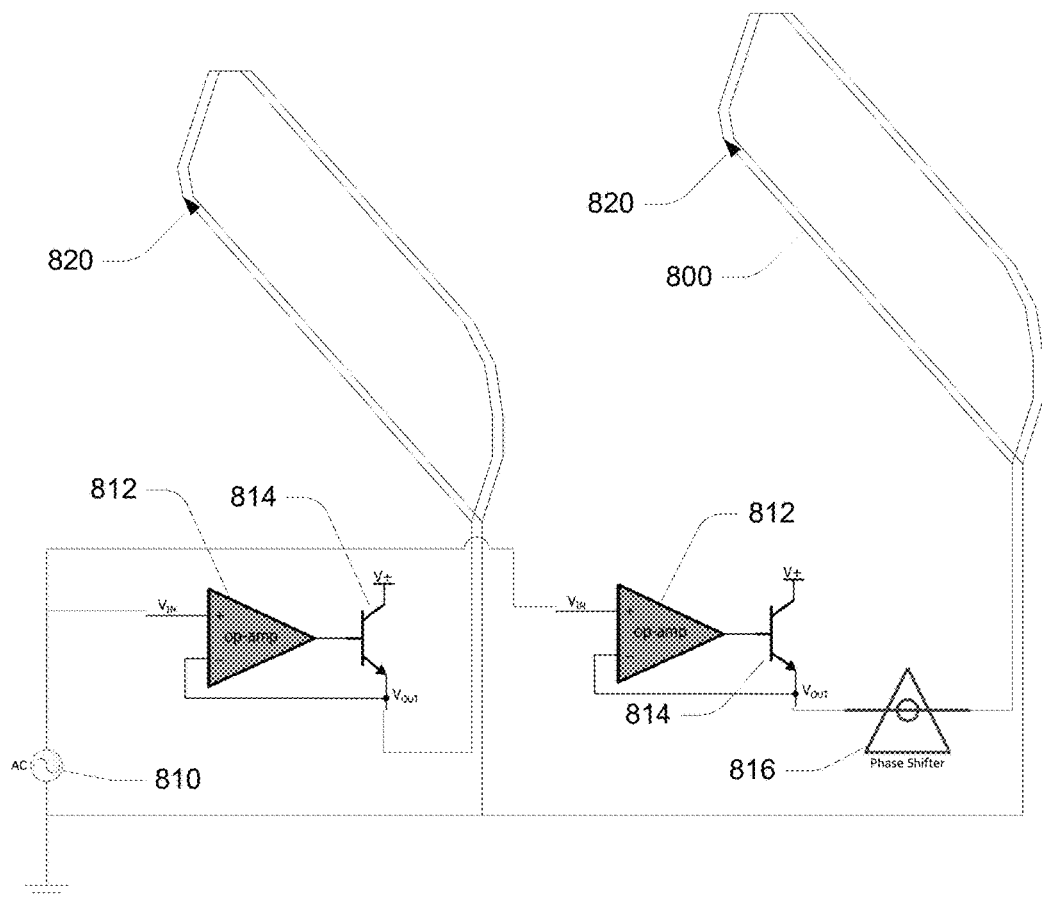
FIG. 8 is a circuit diagram illustrating an example of antennas formed by conductive coils wound about bedrails.

Conductive coils are wound about respective ones of the bedrails 502 to form the antenna 124. As shown in FIG. 8, in some examples the antenna 124 may include two coils 800 wound about two respective bedrails 502 that driven in phase with one another. Further, the coils are wound to be tuned to a predetermined frequency in some embodiments. Each bedrail 502 may be wound with a coil 800 to create an antenna 124 that may be tuned for a specific frequency, 13.56 MHz, for example. There may be one or more windings. External matching components such as inductors and capacitors may be used to tune the coil. Coils may be wound about other patient-support elements of the bed such as the frame, the mattress support, the headboard, or the footboard, for example, or they may be in the vicinity, such as on the wall, ceiling or floor. Each of the coils 800 is connected to a circuit including an operational amplifier 812 connected to a power source 810. The output of the amplifier 812 is connected to the bedrail 800 via a transistor 814. In the illustrated example, one of the coils 800 is connected to a phase shifter 816, which will tend to cause the phase of the two coils 800 to match (when the phase shifter is set to zero), despite small differences in impedance of the coils, because the coils are in the feedback loop of the amplifiers 812 and each amplifier 812 is referenced to the same AC signal source 810. The transistor 814 at the output acts as a current amplifier and provides additional current driving capability. Other driving circuits, such as the OBID i-scan® ID ISC-.DAT from FEIG electronic may be used. The phase shifter 816 allows one coil 800 to be driven at an arbitrary phase compared to the AC signal source 810. If the coils 800 are generally circular with radius, r, spaced a distance r-apart, and driven with currents in-phase as indicated by the arrows 820 then a Helmholtz configuration is achieved where the axial magnetic field is relatively uniform. Even without the Helmholtz configuration, multiple magnetic or electric field antennas may be used to create an array. For example, the bed 500 shown in FIG. 5 includes several rails 502, each of which could have a coil thereabout to create antennas. The magnetic field may be directed by altering the phase of one antenna with respect to another and/or selecting different antennas. For example, if antennas are built into each bedrail 502 of the hospital bed 500 and also the footboard 510, then any of five antennas may be energized with different phases and amplitudes to steer the antenna beam. Small, antennas and/or small, stand-alone NFC reader devices 130 may be used to capture NFC tag data in corners or other areas where coverage by the large antennas is weak. Alternately, an array may be implemented where a large number of small NFC readers 130 is placed about the person-supporting device 120. This allows each NFC reader 130 to be queried independently, including simultaneously, and each can upload data to a network 910. Fitting coils to a person-supporting element may result in antennas that are described more accurately as oblong, for example more in the shape of an ellipse or rectangle versus circular. In the transformation of a conductive coil from a circle to an oblong shape, the overall field may decrease primarily in the direction in which the diameter of the coil is decreased, i.e., along the direction the semi-minor axis for an ellipse. This specification will use the term semi-major axis to mean the dimension of an oblong shape that is larger and semi-minor axis to mean the dimension of an oblong shape that is smaller. Other antenna configurations, such as one or more conductive plates, such as those used with UHF tags, may be used. In a single plate configuration, the bedframe or other large conductive mass may serve as a ground plane. In a two-plate configuration, one of the plates may serve as a ground plane.

In some examples, the provision of the person-supporting device 120 having a power supply and antenna for the NFC interrogation device 122 facilitates continuous monitoring of the contact sensor 112, rather than a single reading by a caregiver using a hand-held interrogation device. As noted above, the interrogation device 122 incorporated into the person-supporting device 120 may have wired and/or wireless communication in addition to the NFC device. Thus, rather than requiring a caregiver to place a conventional NFC interrogation device very close to the sensor 112 to obtain sensor data, the interrogation device 122 may receive data from the sensor 112, and relay the received data to another device, such as a tablet or other handheld device carried by a caregiver.

Figure 9:
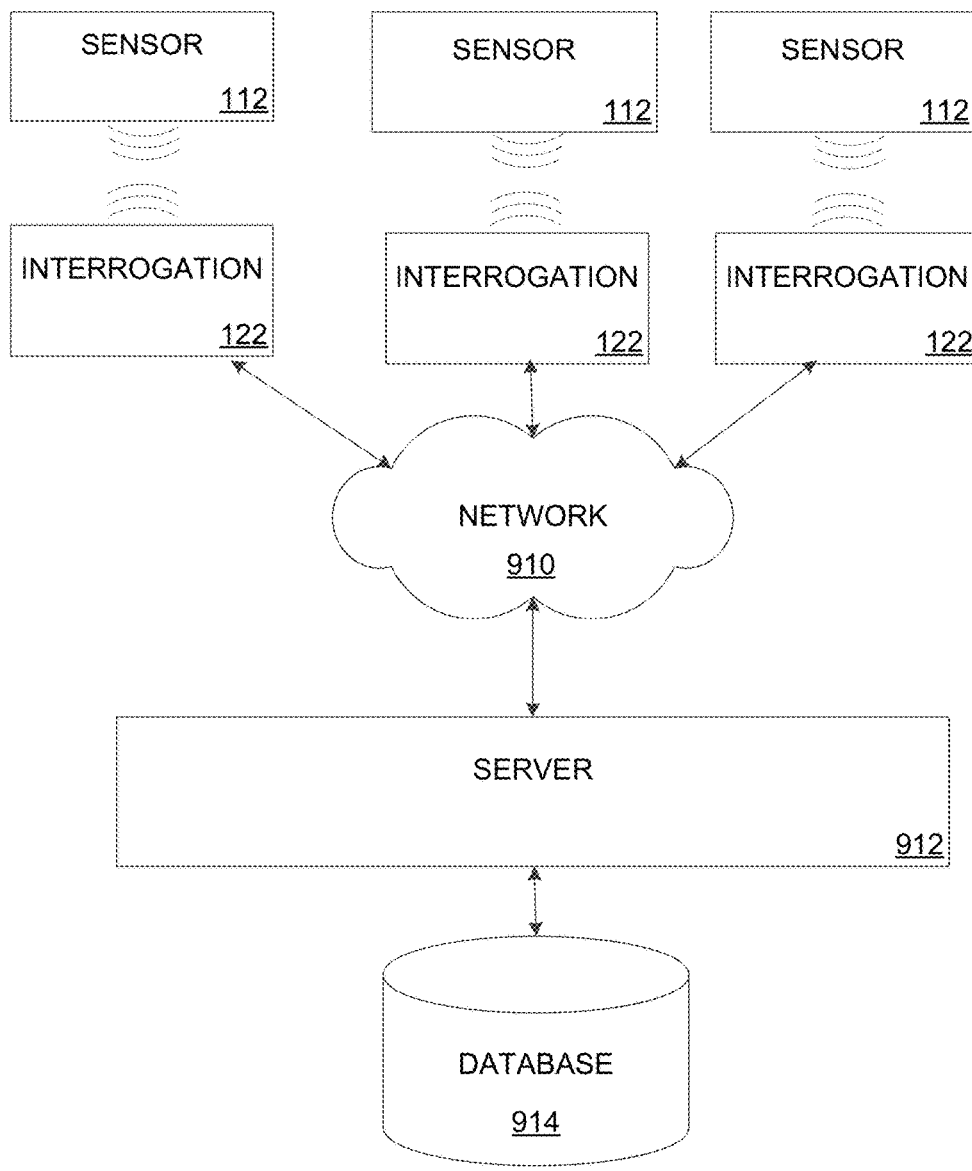
FIG. 9 is a block diagram illustrating an example network arrangement.

Some disclosed person-supporting devices 120 are further connectable to a network, such as a hospital network or the internet. An example network arrangement is shown in FIG. 9, where several interrogation devices are connected to a network 910. Patient parameters from the patient sensors 112 are received by the interrogation devices 122, and are transmitted to a network 910 by any suitable wired or wireless communication, such as the connection that exists in a patient support structure disclosed, for example, in U.S. Pat. No. 8,082,160 (incorporated by referenced in its entirety) or in a patient monitor such as the CVSM patient monitor available from Welch Allyn Inc., Skaneateles Falls, N.Y. Data backhaul may be supported by the system: data from the interrogation devices 122 may be transmitted to a server computer 912 via the network 910 and saved to a database 914. In some embodiments, the server computer 912 includes a data management system such as the Connex® data management systems available from Welch Allyn Inc., Skaneateles Falls, N.Y. In some of these embodiments, the person-supporting device has knowledge of the patient, such as the room number, patient name, patient ID or other identifier. The system may use this information to automatically tag the physiological data to allow filing in a medical records system such as an EMR or EHR. In other embodiments, the sensor may be provisioned with a patient identifier for example, an encrypted version of the patient ID, by writing across the NFC RF interface. In yet another embodiment, the sensor may encrypt the some or all of the patient data, including patient identifiers using cryptographic methods known to those familiar with the art, such as public-key cryptography.

In further examples, the person-supporting device 120 may further include additional sensors, such as a non-contact or contactless sensor, that is, a sensor that does not contact the body of the patient 110 (such as mounting onto a garment). For instance, the substrate 600 shown in FIG. 6 may include a contactless sensor 610 to measure additional patient parameters.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A sensor system, comprising: a person-supporting device including an antenna and a near-field communication (NFC) interrogation device; a first sensor configured to measure a physiological parameter of a person associated with the person-supporting device; wherein the NFC interrogation device and the antenna are configured to establish wireless communication with the first sensor and receive data from the first sensor from a distance of at least 10 inches; and wherein: the first sensor includes a contact sensor configured to measure a first physiological parameter of the patient while contacting the patient; the person-supporting device includes a substrate having the antenna mounted thereon; and the sensor system further comprises a second sensor mounted on the substrate, wherein the second sensor includes a contactless sensor configured to measure a second physiological parameter of the patient without contacting the patient.

2. The sensor system of claim 1, wherein the person-supporting device includes at least one of a bed, a patient lift, and a wheel chair.

3. The sensor system of claim 2, wherein the person-supporting device includes a bed having a plurality of bedrails spaced apart from one another and extending from the bed, and wherein the antenna includes a plurality of coils wound about respective bedrails.

4. The sensor system of claim 3, wherein the plurality of coils includes first and second coils driven at a controlled phase of the first coil with respect to the second coil.

5. The sensor system of claim 1, wherein the antenna includes a conductive coil defining a semi-major axis of at least one-tenth wavelength.

6. The sensor system of claim 1, wherein the antenna is integrated into the person-supporting device.

7. The sensor system of claim 1 wherein the person-supporting device provides power to the NFC interrogation device.

8. The sensor system of claim 1, wherein the first sensor includes a contact sensor configured to measure the physiological parameter of the patient while contacting the patient.

9. The sensor system of claim 1, wherein the NFC interrogation device is mounted on the substrate.

10. The sensor system of claim 1, wherein the antenna comprises a conductive plate.

11. A person-supporting system, comprising: a plurality of person-supporting elements; at least one antenna attached to at least one of the person-supporting elements; and an amplifier connected to the at least one antenna; and the person-supporting system, further comprising: a near-field communication (NFC) interrogation device, wherein the NFC interrogation device and the antenna are configured to establish communication with and receive data from a first sensor configured to measure a physiological parameter of a patient.

12. The person-supporting system of claim 11, further comprising a bed, wherein the plurality of person-supporting elements includes first and second bedrails, and wherein the at least one antenna includes first and second coils wound about the bedrails.

13. The person-supporting system of claim 12, wherein the first and second coils are driven with a specific phase one to another.

14. The person-supporting system of claim 11, wherein the plurality of coils are wound to be tuned to a predetermined frequency.

15. The person-supporting system of claim 11, wherein the plurality of coils are arranged to achieve a Helmholtz configuration.

16. An interrogation device for receiving data from a patient sensor, comprising: a person-supporting device; a near-field communication (NFC) reader device mounted to the person-supporting device and configured to establish wireless communication with a first sensor and receive data from the first sensor; wherein the person-supporting device provides data backhaul; and wherein the person-supporting device includes a substrate having a contact sensor configured to measure a first physiological parameter of the patient while contacting the patient and a contactless sensor configured to measure a second physiological parameter of the patient without contacting the patient.

17. The interrogation device of claim 16, wherein the person-supporting device includes a bed having a plurality of person-support structures spaced apart from one another and extending from the bed, and wherein the person-support structures include at least one antenna.

* * * * *